(12) United States Patent
Blair et al.

(10) Patent No.: US 10,451,617 B2
(45) Date of Patent: Oct. 22, 2019

(54) METHOD FOR CAPTURING, METHOD FOR DETECTING AND KIT FOR CAPTURING A MOLECULE IN A SAMPLE

(71) Applicants: Centre National de la Recherche Scientifique (CNRS), Paris (FR); Institut Polytechnique de Grenoble, Grenoble (FR)

(72) Inventors: Guillaume Blair, Magland (FR); Luiz Fernando Zanini, Grenoble (FR); Gilbert Reyne, Marseilles (FR); Nora Dempsey, Grenoble (FR); Marianne Weidenhaupt, St Joseph de Rivière (FR); Franz Bruckert, Grenoble (FR); Orphée Cugat, Poisat (FR)

(73) Assignees: Centre National de la Recherche Scientifique(CNRS), Paris (FR); Institut Polytechnique de Grenoble, Grenoble (FR)

( * ) Notice: Subject to any disclaimer, the term of this patent is extended or adjusted under 35 U.S.C. 154(b) by 475 days.

(21) Appl. No.: 14/761,087

(22) PCT Filed: Nov. 26, 2013

(86) PCT No.: PCT/EP2013/074736
§ 371 (c)(1),
(2) Date: Jul. 15, 2015

(87) PCT Pub. No.: WO2014/111187
PCT Pub. Date: Jul. 24, 2014

(65) Prior Publication Data
US 2015/0355174 A1  Dec. 10, 2015

(30) Foreign Application Priority Data

Jan. 17, 2013  (FR) ...................................... 13 50421

(51) Int. Cl.
*G01N 33/543*  (2006.01)
*G01N 27/74*  (2006.01)
*H01F 1/00*  (2006.01)

(52) U.S. Cl.
CPC ....... *G01N 33/5434* (2013.01); *G01N 27/745* (2013.01); *G01N 33/54333* (2013.01); *H01F 1/0054* (2013.01)

(58) Field of Classification Search
None
See application file for complete search history.

(56) References Cited

U.S. PATENT DOCUMENTS

| 6,432,630 | B1 * | 8/2002 | Blankenstein | B01D 57/02 422/186 |
| 2002/0110825 | A1 * | 8/2002 | Spicer | B01L 3/5085 435/6.13 |
| 2004/0018611 | A1 * | 1/2004 | Ward | B01L 3/502761 435/287.2 |

FOREIGN PATENT DOCUMENTS

WO  WO 2007/125129  11/2007
WO  WO 2013/174881  11/2013

OTHER PUBLICATIONS

Issadore et al., Self-assembled magnetic filter for highly efficient immunomagnetic separation, Lab on a Chip, 11 (1), pp. 147-151, published on Jan. 7, 2011.*

(Continued)

*Primary Examiner* — Rebecca L Martinez
(74) *Attorney, Agent, or Firm* — Young & Thompson

(57) ABSTRACT

A method for capturing a molecule in a sample, comprising mixing the sample with magnetic particles. Each of the particles being coupled with an element capable of binding selectively to the molecule for capture, so as to form at least one complex comprising a magnetic particle. The element and the molecule bound to the element, immobilizing the at (Continued)

least one complex on a support comprising ordered magnetic field microsources.

17 Claims, 11 Drawing Sheets

(56) References Cited

OTHER PUBLICATIONS

D. Issadore et al., Self-assembled magnetic filter for highly efficient immunomagnetic separation, Lab Chip, 2011, 11,147.
Luiz Fernando Zanini "Bio-Mag-MEMS Autonomes bases sur des aimants permanents" (thesis), 166 pages.
Blaire Guillaume et al. "Hybrid Bio-Mag-MEMS combining magnetophoresis and dielectrophoresis", The European Physical Journal B, vol. 86, No. 4 (2013).
Hua Kuang et al., "A One-Step Homogenous Sandwich Immunosensor for *Salmonella* Detection Based on Magnetic Nanoparticles (MNPs) and Quantum Dots (QDs)", Int. J. Mol. Sci. 14: 8603-8610 (2013).
N.M. Dempsey et al., "High Performance Hard Magnetic NdFeB Thick Films for Integration into Micro-Electro-Mechanical Systems," App. Phys. Lett. 90, 092509, pp. 1-3, (2007).
A. Walther et al., "Micro-Patterning of NdFeB and SmCo Magnet Films for Integration into Micro-Electro-Mechanical-Systems," J. Magn. Mag. Mat 321, 590-594 (2009).
M. Kustov et al., "Magnetic Characterization of MicroPatterened Nd—Fe—B Hard Magnetic Films Using Scanning Hall Probe Microscopy," J. App. Phys. 108, 063914, pp. 1-7 (2010).
F. Dumas-Bouchiat et al., "Thermomagnetically Patterend Micromagents," App. Phys. Lett. 96, 102511, pp. 1-3, (2010).
Osman et al., "Monitoring the endocytosis of magnetic nanoparticles by cells using permanent micro-flux sources," Biomed Microdevices (2012), 14:947-954.

* cited by examiner

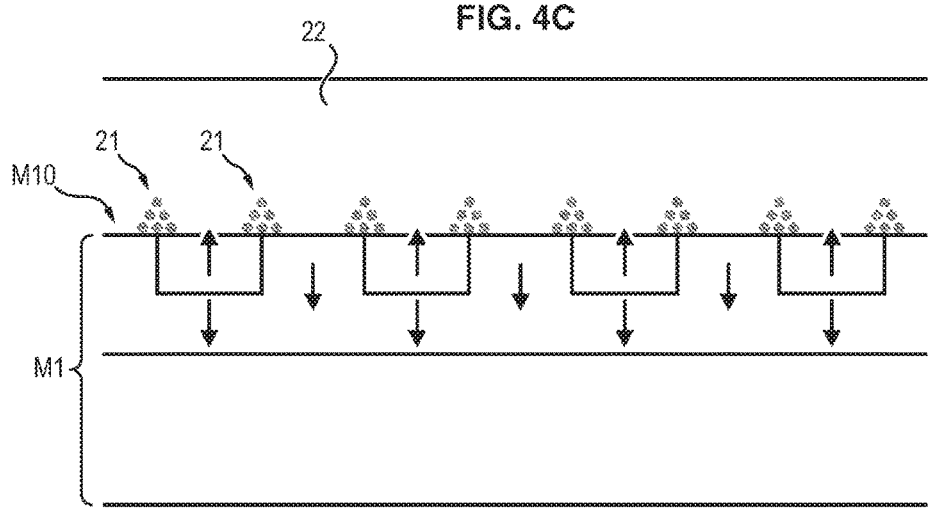
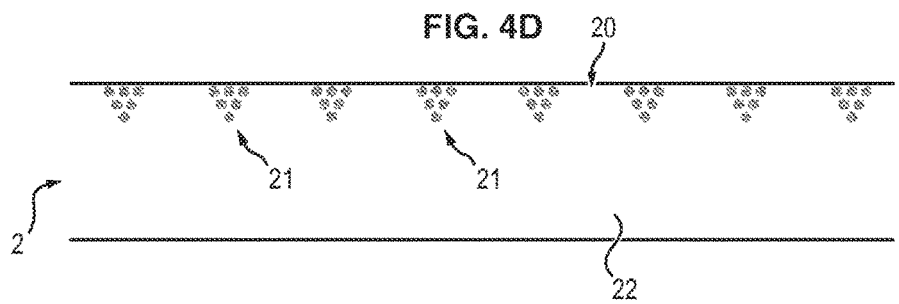
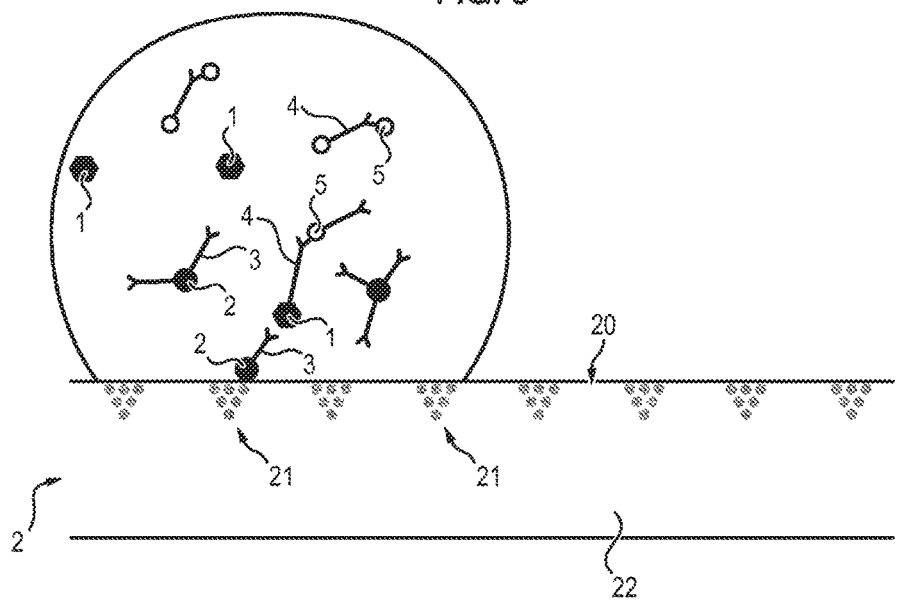

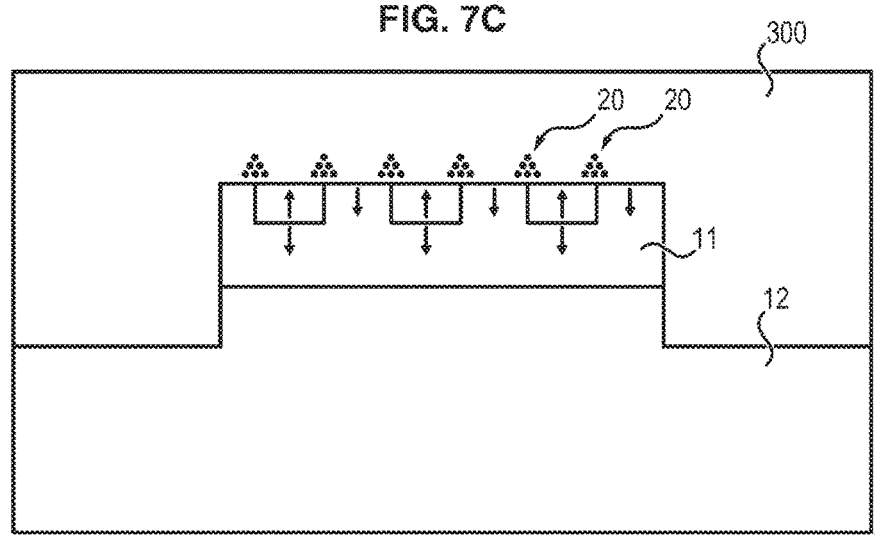
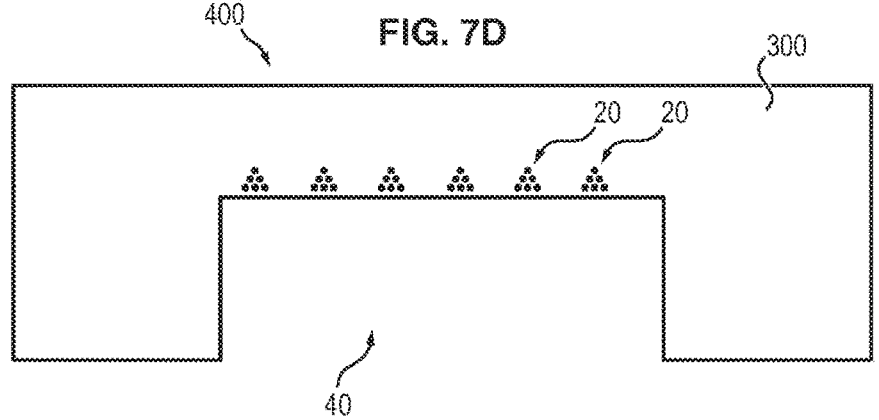
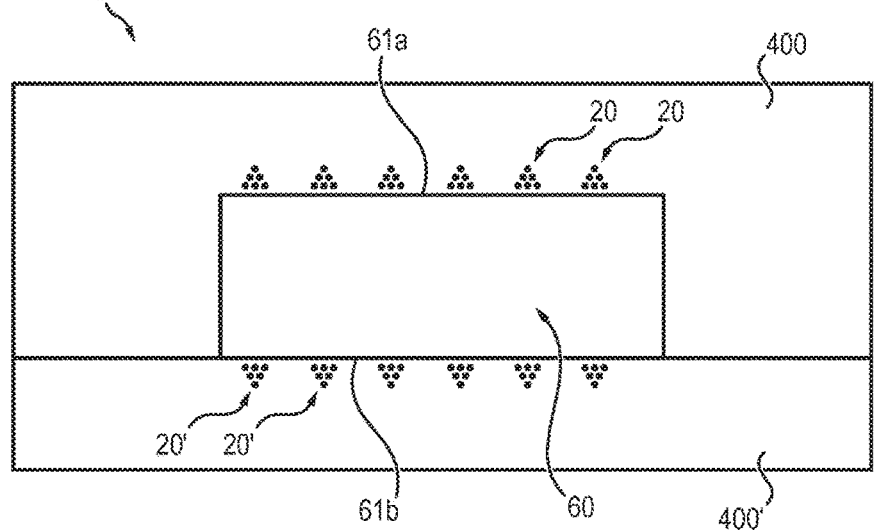

METHOD FOR CAPTURING, METHOD FOR DETECTING AND KIT FOR CAPTURING A MOLECULE IN A SAMPLE

CROSS REFERENCE TO RELATED APPLICATIONS

This application is a U.S. National Stage of International Application Number PCT/EP2013/074736, filed Nov. 26, 2013, which claims the benefit of the priority date of French Patent Application FR 1350421, filed Jan. 17, 2013, the contents of which are herein incorporated by reference.

FIELD OF THE INVENTION

The present invention relates to a method for capturing and a method for detecting, in particular by immunoassay, a molecule in a sample, said molecule for capture or for detection being typically an antigen or an antibody. The invention also relates to a kit for capturing a molecule that is adapted for the implementation of said methods.

BACKGROUND OF THE INVENTION

ELISA assay (acronym of the term "Enzyme-Linked ImmunoSorbent Assay") is commonly used for quantitative diagnosis of molecular markers (antigens or antibodies) which are present in fluids, biopsies, cultures, or any other sample.

This assay is used more particularly for diagnosing infections (HIV, HPV, etc.), the condition of the cardiovascular and immune system (Troponin C, specific antibodies, etc.), and the presence and development of cancers (PSA, CEA, etc.).

This technique, which is presently the most robust and most widespread of methods of diagnosis, is nevertheless not without drawbacks: specifically, its complexity, the use of expensive automated instruments, and its duration, which may extend to several hours.

ELISA assay is a heterogeneous-phase immunoassay technique, meaning that it requires a solid support (typically, a titration plate comprising a plurality of wells) to which a molecule is attached beforehand, said molecule being adapted for capturing the molecule to be assayed.

When the molecule of interest has been captured on said support, washing allows the remainder of the sample to be removed and the step of detecting and quantifying said molecule to be commenced.

For example, in the case of the "sandwich" ELISA assay, for assaying an antigen in a solution, the surface of the support is covered with a specified amount of a capture antibody, said antibody being adapted for binding to the target antigen.

The solution likely to contain said antigen is then applied to the support; said antigen then binds to the capture antibody sited on the surface of the support.

The support is subsequently washed so as to remove the unbound antigen possibly remaining in the solution.

Deposited next on the support is a solution containing an antibody called a detection antibody, which is adapted for binding to the antigen fixed on the support, and which, moreover, is coupled to an enzyme.

A further washing step is implemented, so as to retain the antigen bound to the detection antibody on the support, said antibody being itself coupled to the enzyme.

Lastly, for the detection and quantification of the antigen, a substrate is deposited on the support, this substrate being converted by the enzyme into a detectable signal (for example, a color, or spectroscopically, in other words by emission of fluorescence) that is representative of the binding between the antigen and the detection antibody.

Said signal may be observed with the naked eye or by means of an instrument, such as a spectrophotometer.

ELISA assay encompasses various implementations, but they all include multiple steps of grafting and incubation which are separated by washing steps.

The substantial duration of ELISA assay is due essentially to the succession of the various steps.

Variants of this assay which employ magnetic microbeads have already been described.

The article by D. Issadore et al., Self-assembled magnetic filter for highly efficient immunomagnetic separation, Lab Chip, 2011, 11, 147 thus describes a method for capturing a molecule in a sample by circulating said sample within a fluid microchannel arranged below a polydimethylsiloxane (PDMS) matrix in which magnetic grains of NdFeB have been immobilized.

Owing to the method of manufacture employed for said support, the grains are distributed randomly within the thickness of the matrix, and their magnetic orientation is random.

Each grain generates a magnetic field gradient which is capable of attracting magnetic particles with a diameter of 1 µm that are coupled to the molecules to be detected, to form complexes.

However, the smaller the size of the particles to be captured, the less effective a magnetic field gradient of this kind, meaning that this device performs less well for the capture of magnetic particles with sizes smaller than 1 µm, of the order of 500 nm or less, for example, and especially of nanoparticles.

Furthermore, the capture of the magnetic particles is relatively slow.

This capturing step is followed by washing of the surface of the PDMS matrix and then by fluorescence detection of the complexes immobilized on said surface.

SUMMARY OF THE INVENTION

It is an aim of the invention to provide a method for detecting a molecule such as antigen, or an antibody, that involves a limited number of steps, or even a single step, and that is substantially shorter than the known assays.

This method ought, moreover, to be compatible with the apparatus already used by biologists, such as titration plates, fluorimeters, multichannel pipettes, so as to be able to be implemented directly in analysis and research laboratories.

In accordance with the invention, a method is provided for capturing a molecule in a sample, comprising the following steps:

mixing said sample with magnetic particles, each of said particles being coupled with an element capable of binding selectively to said molecule for capture, so as to form at least one complex comprising a magnetic particle, said element, and said molecule bound to said element, immobilizing said at least one complex on a support comprising ordered magnetic field microsources.

By "ordered" is meant that the magnetic field microsources are distributed close to that surface of the support that is intended for contact with the sample according to a specified pattern, and that they also exhibit a specified magnetic orientation. Such ordering necessarily excludes random orientation and/or distribution of the magnetic field microsources.

According to one embodiment of the invention, the method includes a step of washing said support to remove said sample, the complexes being retained on the support by the magnetic field microsources.

According to another embodiment of the invention, the complexes may be detected at the level of the ordered magnetic field microsources, without washing of the support beforehand.

A molecule for the purposes of the present text is a protein, in particular an antibody, a nucleic acid (DNA or RNA), a virus, a bacterium, an antigen, a cell, and, generally, any biological object.

The magnetic particles preferably have a diameter of between 5 nm and 1 µm, more preferably between 5 nm and 500 nm, or even between 5 and 50 nm.

According to one embodiment, the support comprises a nonmagnetic matrix comprising a plurality of ordered, three-dimensional agglomerates of magnetized micro- or nanoparticles made from a hard or soft magnetic material, said agglomerates forming the magnetic field microsources.

According to another embodiment, the support comprises a nonmagnetic matrix comprising a plurality of magnetic microcoils ordered according to a specific pattern relative to the surface of the support.

Said nonmagnetic matrix may be flexible.

Moreover, said nonmagnetic matrix may be made of a translucent or transparent material.

According to one implementation of the invention, the molecule for capture is an antigen and the element capable of binding to said molecule is a receptor antibody for said antigen.

Said mixture is optionally admixed with a detection antibody which carries a fluorescent, luminescent, or colorimetric label, said antibody being capable of binding to the antigen bound to the antibody coupled to the magnetic particle. The detection antibody may also be labeled with an enzyme that catalyzes a redox reaction, permitting electrochemical detection.

According to another implementation of the invention, the molecule for capture is an antibody and the element capable of binding to said molecule is an antigen which is recognized by said antibody.

According to one embodiment, the support is a titration plate comprising a plurality of wells, the magnetic field microsources being arranged in a wall of each of said wells, the mixture being deposited in at least one of said wells.

According to another embodiment, the support is a flat plate comprising a plurality of magnetic field microsources, the mixture being deposited in the form of at least one drop on said support.

According to another embodiment, the support is a microfluidic channel in which at least one of the walls comprises magnetic field microsources.

A further subject of the invention concerns a method for detecting and, where appropriate, for quantifying a molecule, in which said molecule is captured on a support by implementing the capture method described above, and then a step of detecting said molecule is performed.

The molecule captured on the support may be detected by fluorescence, luminescence, colorimetry, electrochemistry and/or radiometry.

A first advantage of this method is the significant reduction in the number of steps prior to the detection and, where appropriate, the quantification (only one step of mixing and, optionally, one washing step being required), relative to the known immunoassays (the standard sandwich ELISA assay comprising six steps at the minimum).

The reason is that the attraction of the magnetic particles by the magnetic field microsources firstly enables rapid extraction of the objects associated with said particles, and secondly ensures more effective washing (in cases where such washing is implemented), with the magnetic forces of interaction firmly retaining the immobilized complexes it is desired to preserve.

Furthermore, this method offers an alternative to the set of possible implementations of ELISA assay, and can be implemented for performing sandwich assays, but also direct assays or competition assays, by selecting the appropriate antigens and antibodies.

This method can also be adapted for carrying out immunoprecipitation assays.

Another advantage of this method is its great simplicity of implementation and its low cost, associated with the lack of any need for an external energy source for the capture of the complexes and for washing.

Insofar as it is possible to omit the washing step prior to detection, the method may include just a single step of mixing in contact with the support comprising the ordered magnetic field microsources.

Owing to this simplicity, the method would be able to be implemented in an integrated assay device of "point-of-care" type.

Another subject of the invention relates to a kit for capturing a molecule, comprising a support which comprises ordered magnetic field microsources, and a plurality of magnetic particles.

Said magnetic particles have a functionalized surface adapted for the coupling of an element capable of binding selectively to said molecule.

According to one embodiment, the support is a titration plate comprising a plurality of wells, the magnetic field microsources being arranged in at least one wall of each well.

According to one embodiment, the support is a flat plate with the magnetic field microsources arranged on its surface.

According to one embodiment, the support is a fluid microchannel, the magnetic field microsources being arranged on the surface of at least one of the walls of said microchannel.

Another advantage of this method is that it allows detection without washing of the captured molecule, owing to the knowledge by the practitioner of the regions in which the magnetic particles are captured. The specific signal is obtained by subtracting a signal corresponding to the non-specific capture of the molecules from the total signal.

According to one embodiment, the molecules are detected by fluorescence, luminescence, or colorimetry by virtue of a detection antibody. An image of fluorescence, luminescence, or absorbance of the surface carrying the micromagnets makes it possible to determine the specific and nonspecific signals. The total signal corresponds to the presence of molecules in regions of strong magnetic field gradient; the nonspecific signal corresponds to the presence of molecules in the regions of weak magnetic field gradient.

According to another embodiment, the molecules are detected by electrochemistry, by virtue of a detection antibody coupled to an enzyme having redox properties. Electrodes are disposed on the surface of the support in order to allow the total and nonspecific signals to be measured. The total signal corresponds to electrodes disposed at the ordered magnetic field microsources; the nonspecific signal corresponds to electrodes disposed in regions without magnetic field microsources.

BRIEF DESCRIPTION OF THE DRAWINGS

Further characteristics and advantages of the invention will become apparent from the detailed description hereinafter, with reference to the attached drawings, in which:

FIGS. 4A to 4D illustrate schematically the various steps in the method called "Micro-Magnetic Imprinting", FIG. 5 illustrates an embodiment of the invention in which the mixture is deposited on a flat support, in the form of a drop, FIGS. 7A to 7E illustrate a method for producing a fluidic microchannel comprising magnetic field microsources, allowing the method according to the invention to be implemented.

DETAILED DESCRIPTION

Figure 1A:
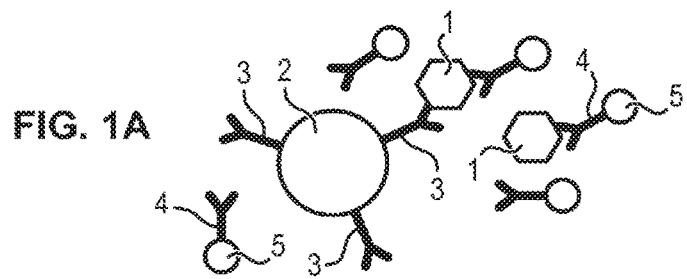
FIGS. 1A to 1C are schematic views of steps in implementing the detection method according to one embodiment.
Figure 1B:
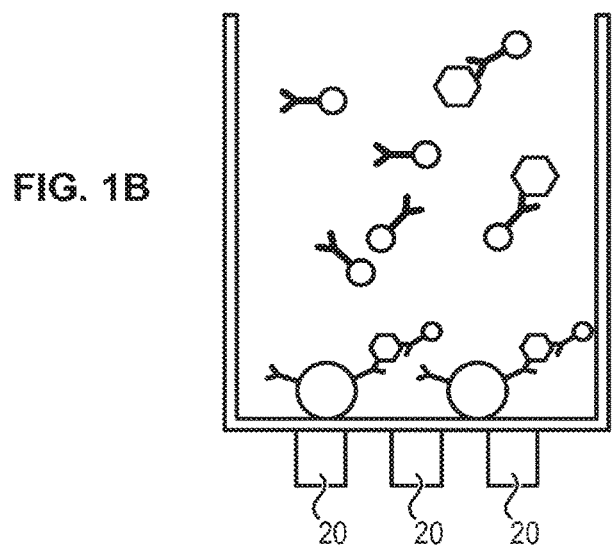
Figure 1C:
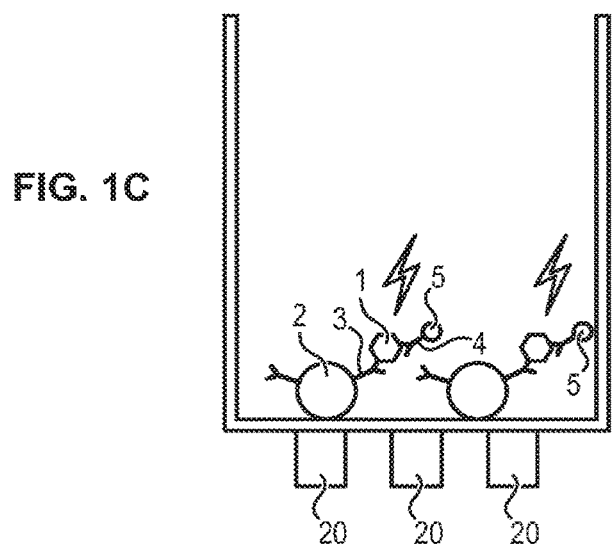

FIGS. 1A to 1C illustrate schematically the main steps in the detection method according to one embodiment of the invention, corresponding to a sandwich immunoassay.

In this case, the molecule for detection and assay is an antigen.

According to this method, a mixture is made of the following elements:
- a sample likely to contain the antigen 1 whose presence it is desired to detect and quantify,
- magnetic particles 2 coupled beforehand to a capture antibody 3, in other words a receptive protein specific for the antigen to be detected, in excess relative to the antigen,
- a detection antibody 4 which carries a fluorescent, luminescent or colored label 5, in excess relative to the antigen.

Said label 5 may be carried directly by the detection antibody or indirectly, via an enzyme.

Said mixing is carried out in a container in which, under the effect of the spreading of the various constituents, the antigen 1 binds to the capture antibody 3 coupled to a magnetic particle 2, and then the detection antibody 4 binds to the antigen 1.

A "sandwich" complex is formed accordingly, formed of a magnetic particle 2, the capture antibody 3, the antigen 1, the detection antibody 4, and the label 5.

The bonds between the antigen and the capture antibody, and between the detection antibody and the antigen, are noncovalent bonds.

Conversely, the coupling between the magnetic particle and the capture antibody is a covalent bond.

Said mixture is deposited, by means of a pipette, for example, on a support which comprises ordered magnetic field microsources.

The effect of the magnetic field microsources is to attract the magnetic particles and, consequently, to immobilize the aforementioned complexes on the support, according to a pattern which is closely linked to the ordering of the magnetic field microsources relative to the surface of said support. For example, if the magnetic field microsources are arranged in the form of a chessboard whose two adjacent boxes exhibit magnetizations in opposite directions, the magnetic particles will become immobilized at the junction between two magnetic field microsources, which is the location at which the stray field, and also its gradient, is most intense.

The antigens not bound to the magnetic particles, and the labeled antibodies not bound to the antigen, are not attracted by the magnetic field microsources and remain in suspension in the mixture.

An optional washing step allows these residues to be removed and for only the complexes to be preserved on the support, these complexes being retained by the magnetic field microsources, by interaction with the magnetic particles.

This is because the magnetic force generated on the complexes by the magnetic field microsources (which are capable of generating very strong magnetic field gradients) is greater than the aspiration force exerted during washing.

Accordingly, the molecules of interest, coupled to the magnetic particles, have been captured and held on the support.

However, as set out in detail later on, it is also possible to dispense with the washing step. The reason is that knowledge of the ordering of the magnetic field microsources relative to the surface of the support, and the implementation of an appropriate detection technique, make it possible for the particles trapped by said ordered microsources to be detected, without any need to remove the sample or to wash the surface of the support.

When this capture has been performed, it is then possible to implement a quantification method known to the skilled person, depending on the nature of the labels used.

These quantification methods include fluorescence, luminescence, colorimetry, a RedOX reaction, radioactivity, turbidimetry, magnetic detection by localized GMR magnetic micro- and nanosensors, etc.

The total duration of this assay is typically between 10 and 20 minutes, whereas it is between 2 and 6 hours for an ELISA assay employing the conventional steps of mixing and detecting.

Relative to the ELISA assay, which, as indicated earlier on above, is a heterogeneous-phase immunoassay method, the method according to the invention may be regarded as a homogeneous-phase immunoassay method.

The reason is that the binding between the antigen for assay and the detection antibody takes place within the volume of the sample and not on the surface of the support, said support being intended solely for immobilizing the complexes during the washing which precedes the detection and quantification, or for the purpose of direct detection without washing, as envisaged earlier on above.

The presence, within said volume, of a large number of magnetic particles, with sizes which may be less than that used in the known methods, and the high diffusion coefficient that their small size confers on these particles, increase their probability of encountering the antigens and the detection antibodies.

It should be specified that, although the example given above relates to a sandwich immunoassay, which can replace the conventional sandwich ELISA assay, the method may be adapted so as to offer the same modalities as other immunoassays (of direct ELISA or competitive ELISA type) or other methods involving the capture of a molecule, such as immunoprecipitation.

For example, an immunoprecipitation assay is intended for purifying a specified protein in a sample comprising a plurality of proteins.

This assay employs antibodies adapted to bind selectively to the protein whose detection is desired.

In an assay of this kind, said antibodies are coupled to a plurality of magnetic particles, and said particles are introduced into the sample.

The antibodies bound to the magnetic particles will then bind to the proteins which are specifically recognized.

The proteins which it is wished to isolate are bound to the antibodies, which are themselves coupled to the magnetic particles, thereby forming complexes.

By virtue of the ordered magnetic field microsources, it is then possible to immobilize said complexes on a support and subsequently, where appropriate, to carry out washing in order to remove the rest of the sample.

Conversely, in methods which do not employ magnetic field sources, the antibodies are bound chemically to the well of the titration plate that has been functionalized beforehand.

Relative to the method of D. Issadore et al., the use of a support comprising ordered magnetic field microsources makes it possible, for a given size of magnetic particles, to increase the range of the magnetic field microsources and/or, for a given range, to increase the force exerted on the small-size particles.

The invention consequently allows more rapid and more effective capture.

Moreover, the ordering of the magnetic field microsources makes it possible to carry out detection without necessarily washing the support, something which is not possible when the magnetic field microsources are arranged randomly in the support, since the skilled person is then unable to differentiate the captured particles from noncaptured particles.

Magnetic Particles

The particles employed are magnetic particles with micrometer dimensions (microparticles) or nanometer dimensions (nanoparticles).

Said particles may advantageously be likened to beads.

In the remainder of the text, the particles may therefore be referred to by the term "beads", although their geometry is not a perfect sphere.

Such beads are available commercially in large amounts and at low cost, especially for applications such as magnetic resonance imaging (MRI), hence imposing no burden on the costs of the assay.

Said beads are preferably monodisperse, with the dimensional uniformity of the beads giving them identical properties and hence improving the spreading of the beads within the mixture and their capture by the magnetic field microsources.

In certain cases, the beads are commercialized in a form in which they are dispersed in a nonmagnetic or relatively nonmagnetic matrix, such as a polymer, silica ($SiO_2$), etc.

The beads are preferably biocompatible.

In order to allow the coupling by covalent bonding of an element intended for coupling selectively with the molecule for capture, the surface of the particles is functionalized, with proteins A or G, for example.

In the present text, the term "nanoparticle" denotes an object whose three dimensions are on the nanometric scale, in other words whose characteristic size—for example, the average diameter in the case of a bead—is typically less than 100 nm.

The term "microparticle" denotes an object whose three dimensions are on the micrometric scale, in other words whose characteristic size—for example, the average diameter in the case of a bead—is between 100 nm and 100 µm.

Unless otherwise stated, the term "particle" or "bead" employed in the remainder of the text encompasses both the magnetic nanoparticles and the magnetic micro particles.

Because of their dimensions, the magnetic particles employed exhibit superparamagnetic properties.

It is recalled that the term "superparamagnetic" denotes the property possessed by small-size particles of ferromagnetic or ferrimagnetic material of randomly changing direction of magnetization in the absence of an applied magnetic field, under the effect of thermal agitation.

The characteristic of being superparamagnetic implies that in the absence of external excitational magnetic field, the beads do not have any net magnetic moment, and so do not exhibit mutual attraction, thereby preventing their agglomeration.

Relative to the microparticles, the nanoparticles, when coupled to an antibody, exhibit much higher levels of capture of antigens.

This improvement can be explained by the reduction in scale of the nanoparticles relative to the microparticles.

Accordingly, for a reduction in diameter by a factor of 100 (for example, between a microbead 3 µm in diameter and a nanobead 30 nm in diameter):

the diffusion coefficient is multiplied by 100,
the surface/volume ratio is multiplied by 100,
the number of beads per $m^3$ is multiplied by $10^6$.

Since the capture antibodies attach to the surface of the particles, the increase in the surface/volume ratio makes it possible, for an equal mass of particles, to increase the number of capture antibodies and, consequently, to enhance the sensitivity of the assay.

Moreover, the reduction in the size of the particles increases their diffusion rate in the mixture and therefore allows more rapid formation of the complexes.

Another advantage of the nanoparticles is that they are of equivalent sizes to the biological objects (DNA strands, markers for cancer, specific proteins) that are to be detected.

Accordingly, they are animated with the same Brownian motion as these objects, thereby increasing the capacity for capturing them.

Lastly, the increase in the number of capture antibodies by virtue of the nanoparticles allows the thermodynamic equilibrium in the association reaction to be shifted, and could therefore enable the use of antibodies which are presently disregarded on account of their poorer affinity.

Consequently, although the method according to the invention can be implemented with any size of magnetic particle, preference will be given to selecting particles having a diameter of between 5 nm and 1 µm, more preferably between 5 nm and 500 nm, or even between 5 nm and 100 nm or between 5 and 50 nm.

Magnetic Field Microsources

A magnetic field microsource is understood to be a magnet whose three dimensions are on the micrometric scale—in other words, whose length, width, and thickness are less than 1 mm.

According to one embodiment, said magnetic field microsources are composed of a hard magnetic material which can be magnetized permanently.

This ensures the autonomy of the assay device, in other words making it possible to remove any need for electrical supply or an external magnetic field to allow the capture of the superparamagnetic particles.

However, it is possible to consider said microsources being produced from a soft magnetic material, in which case an external magnetic field source (for example, a permanent magnet or an electromagnet) must be placed in the vicinity of the support for magnetizing the microsources, temporarily or permanently.

The magnetic field gradient is generally the strongest at the periphery of a magnetic field microsource and, where appropriate, at the interface between two differently oriented magnetic field microsources.

The magnetic field microsources used in the invention generate magnetic fields which are comparable to those of currently available macroscopic magnets, in other words with an intensity of the order of 0.1 to $1 \times 10^6$ A/m.

Conversely, the magnetic field gradients measured above the surface of the support may reach $10^6$ T/m, in other words a number of orders of magnitude greater than the gradients generated by macroscopic magnets.

The magnetic forces induced on magnetic particles are much greater than those generated by macroscopic magnets (that is, magnets having at least two dimensions greater than 1 mm), something which may be explained by the change of scale.

Accordingly, the reduction by a factor of 1000 of the magnetic field source (for example, between a cubic magnet with sides of 10 mm and a magnet of 10 µm) has the effect of multiplying by 1000 the magnetic force exerted by the microsource.

Consequently, magnetic field microsources of these kinds are presently the only experimentally proven means allowing effective capturing of nanoparticles.

The inventors have demonstrated experimentally to date that these magnetic field microsources are indeed capable of capturing nanoparticles with a diameter of greater than or equal to 5 nm.

However, the advantage of the magnetic field microsources is not limited to superparamagnetic nanoparticles.

The reason is that, even for microparticles, the increase in the magnetic force relative to that of conventional macroscopic magnets facilitates the capture of complexes comprising the microparticles.

The magnetic field microsources may in particular be produced by one of the following methods.

According to one embodiment of the invention, the microsources are manufactured by micrometer-scale magnetic structuring of a layer of a hard magnetic material.

Production of permanent magnets which perform at micrometer scales may comprise the following two successive steps:

the synthesis of high-performance thick magnetic films, having a thickness of between 1 and 100 µm;

the production of magnetic field microsources (which can be likened to permanent micromagnets) by magnetic structuring of said magnetic film.

Synthesis of Magnetic Films

A physical deposition method by triode sputtering, which allows the application of a magnetic material in thick layers (typically 1-100 µm), is described in N. M. Dempsey et al., App. Phys. Lett. 90, 092509 (2007).

As an example, layers of NdFeB, FePt, and SmCo were synthesized, and possess significant magnetic properties.

Other methods for producing magnets in layers may be envisaged, more particularly electrolytic deposition, sol-gel deposition, evaporative deposition, pulsed-laser deposition, etc.

It is also possible to glue a layer of magnetic material to a substrate.

Materials which may be employed in order to form these layers are hard magnetic materials, which can subsequently be magnetized permanently.

Among the materials adapted to such use, mention may be made of magnets based on rare earths, of formula RFeB (where R consists essentially of Nd, Pr, Tb, Dy, or mixture of two or more of these elements), RCo or RCoCu (1/5-type crystallographic structure), RCoCuFe (1/7- or 2/17-type crystallographic structures), RFeN (where R consists essentially of Sm), alloys of a transition metal from the 3d series (Fe, Co, Ni) with a noble metal (Pt or Pd as majority element), ferrite magnets, and MnBi, MnAl, MnGa, FeGa, and AlNiCo magnets.

According to one advantageous embodiment, the hard magnetic material is selected from the classes of NdFeB, SmCo, and FePt.

Furthermore, the generation of substantial magnetic fields and of substantial magnetic field gradients requires magnetic microstructuring of the layer of hard magnetic material. It is this structuring which ensures the ordering of the magnetic field microsources.

With particular advantage, said layer may be microstructured magnetically by one of the two techniques presented below.

Magnetic Structuring by "Topographic" Method

This technique involves pre-application structuring of the substrate on which the hard magnetic material is subsequently applied, and/or direct structuring of the magnetic layer.

The dimensions of the topographical structuring determine the dimensions of the resulting micromagnets.

Each portion of magnetic layer engraved and/or deposited on a microprojection or in a microcavity in the substrate may be compared with an independent magnetic element.

It should be noted that steps of planarizing, optical lithography and/or chemical attack may be necessary.

These microelements thus produced are subsequently magnetized according to a selected direction.

They then constitute an assembly of independent micromagnets, all exhibiting the same direction of magnetization [A. Walther et al., J. Magn. Mag. Mat. 321 (2009) 590].

These individual micromagnets, optionally sited at different heights, constitute systems which exhibit very strong magnetic field gradients on micrometric scales [M. Kustov et al., J. App. Phys. 108, 063914 (2010)].

Figure 2:
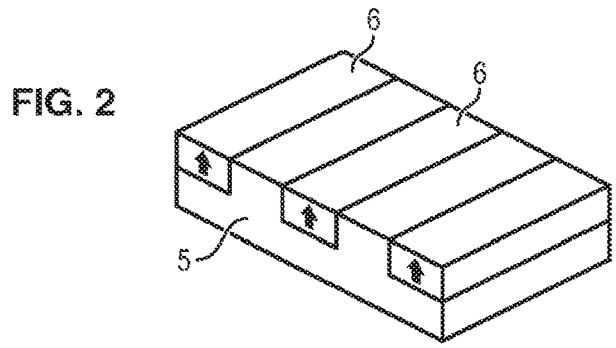
FIG. 2 illustrates schematically a surface structured magnetically so as to form magnetic field microsources.

FIG. 2 illustrates schematically an example of topographical microstructuring.

The substrate 5 comprises a plurality of microcavities which, in this example, are present in the form of parallel trenches.

The hard magnetic material is then deposited in these trenches to form parallelepipedal magnetic regions 6.

The formation of such cavities and the deposition of magnetic material are known per se to the skilled person, and will therefore not be described in detail here.

Where appropriate, polishing is then carried out to give a flat plate whose surface exhibits an alternation of regions of the substrate 5 and regions of hard magnetic material 6.

An external magnetic field is then applied, so as to permanently magnetize the regions 6 of hard magnetic material.

The skilled person has the ability to define the intensity of the magnetic field to be applied in order to obtain the desired magnetization, depending on the materials employed.

Magnetic field microsources of these kinds generate a strong magnetic field gradient and are therefore adapted for the capture and immobilization of magnetic nano- or microparticles.

The dimensions of the microsources are on the submillimeter scale and depend on the precision of the topographic methods employed.

It is self-evident that the forms of these microsources are not limited to parallelepipedal forms; they may therefore be arranged in the form of a chess board, but may also have a circular form, a hexagonal form, etc.

Magnetic Structuring by the Thermo-Magnetic Imprinting Method (or Thermo-Magnetic Patterning)

The principle of structuring by thermo-magnetic patterning is to use a source of heat to bring about local heating of particular zones of a magnetically hard layer and so to create volumes magnetized according to alternate directions, constituting magnetic field microsources.

As an example, a heat source used may be a nanosecond pulse laser by a method the principle of which is described with reference to FIGS. 3A to 3D.

Figure 3A:
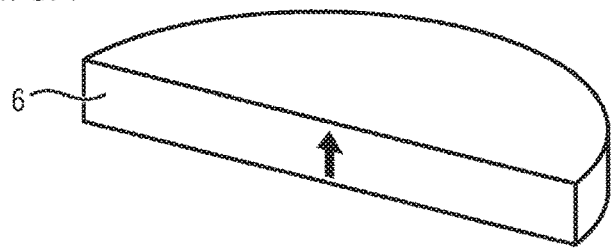
FIGS. 3A to 3D illustrate schematically the various steps in the thermo-magnetic imprinting method allowing a support comprising magnetic field microsources to be produced.

As illustrated in FIG. 3A, a layer 6 of a hard magnetic material is magnetized in one direction and in a given sense (indicated by the arrow).

This layer 6 is subsequently placed in a uniform external magnetic field $H_{ext}$ ($\mu_0 H_{ext} < \mu_0 H_c$) with a direction opposite to the original magnetization direction, and then is locally irradiated by a pulsed laser L (in our case, a KrF excimer laser (248 nm), or a Nd-YAG laser).

Figure 3B:
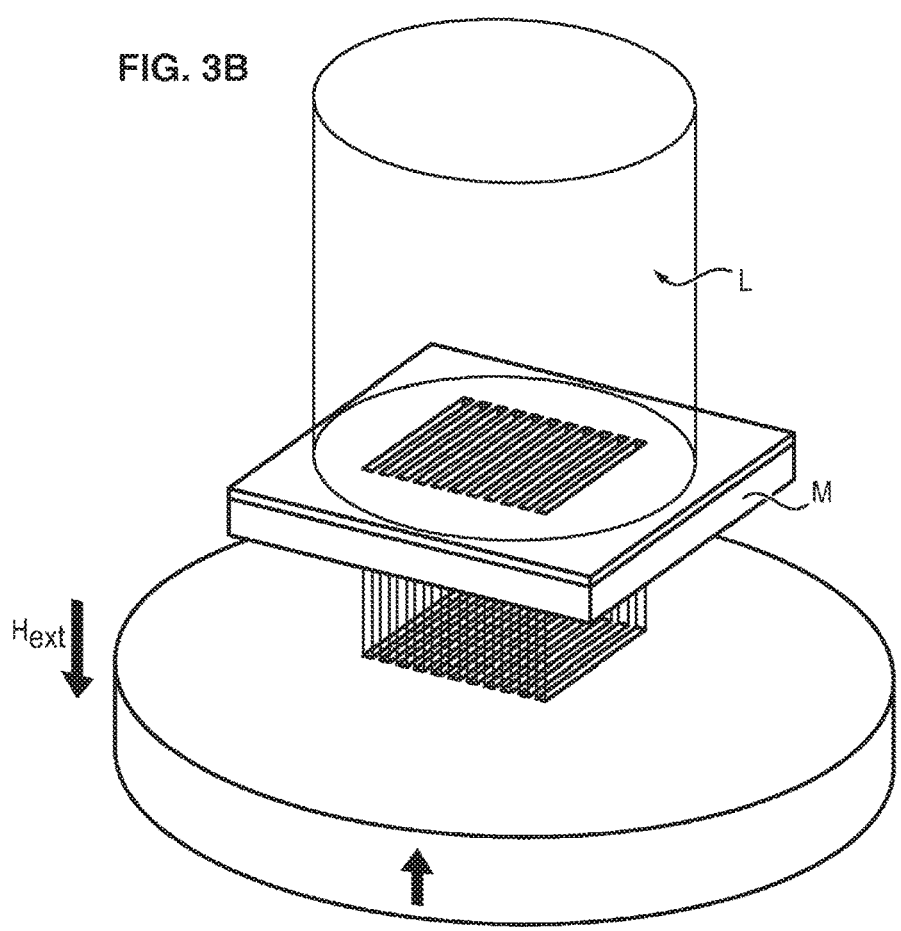

As illustrated in FIG. 3B, said irradiation takes place through a mask M which, in this example, is provided with a certain number of parallel rectangular openings.

Figure 3C:
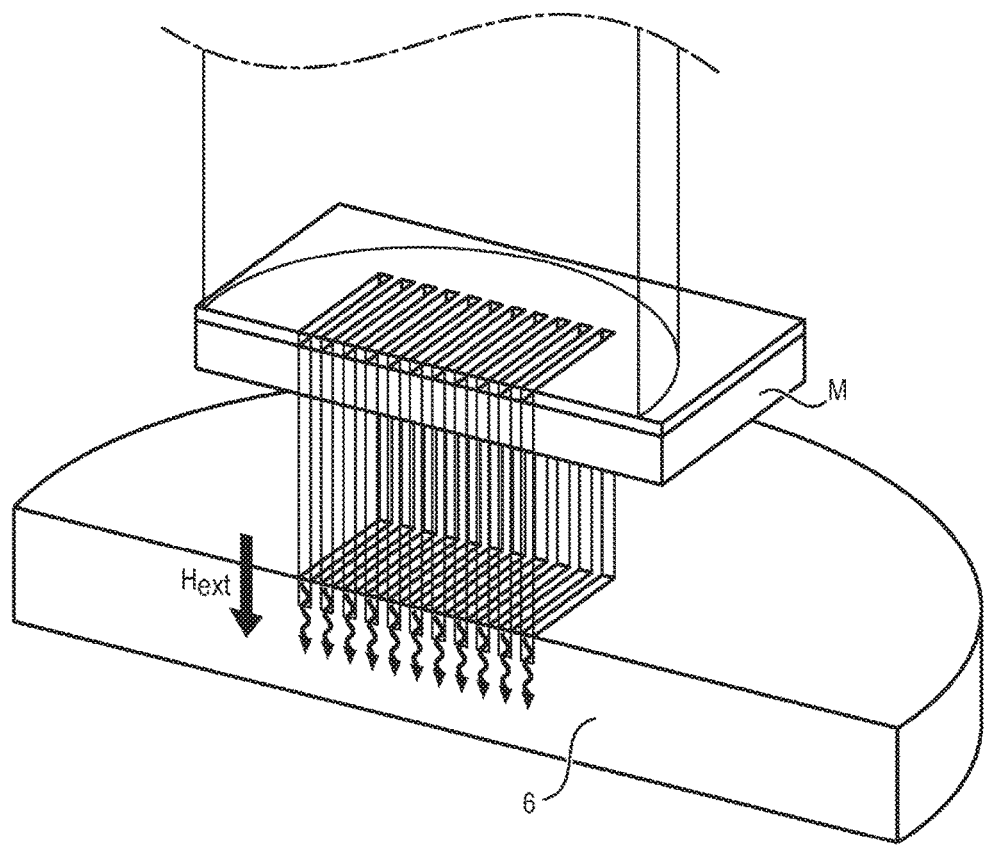

The temperature of the surface of the irradiated zones increases very rapidly, and then the heat diffuses into the material (cf. FIG. 3C).

Given the reduction in the coercive field $\mu_0 H_c$ of a material as its temperature increases, the magnetic reversal of the irradiated zones may be obtained by application of the external magnetic field $H_{ext}$ during the laser pulsing.

Figure 3D:
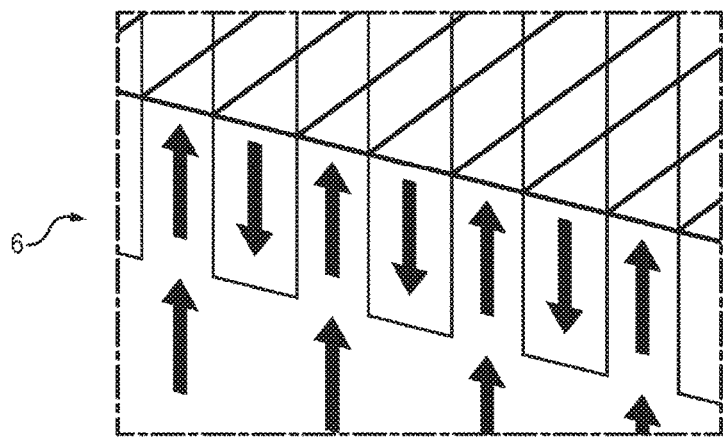

As illustrated in FIG. 3D, the layer is ultimately formed from a network of micromagnets with alternate magnetizations, indicated by the arrows, and with dimensions which are defined by the dimensions of the mask used during laser irradiation.

The systems produced by this method exhibit very strong magnetic field gradients on micrometric scales [M. Kustov et al., J. App. Phys. 108, 063914 (2010)].

For further details regarding this method, reference may be made to the article of F. Dumas-Bouchiat et al., App. Phys. Lett. 96, 102511 (2010).

This principle of thermo-magnetic patterning may be extended to all kinds of hard magnetic layers, including those which exhibit isotropic or in-plane magnetizations.

Micro-Magnetic Imprinting Method

According to another form of implementation of the invention, the microsources 21 are present in the form of ordered agglomerates of nano- or microparticles of a hard magnetic material enclosed within a nonmagnetic matrix, and magnetized.

With particular advantages, said matrix may be made of a flexible material, allowing a flexible support to be obtained.

FIGS. 4A to 4D illustrate steps in one way of manufacturing the support according to the invention.

Figure 4A:
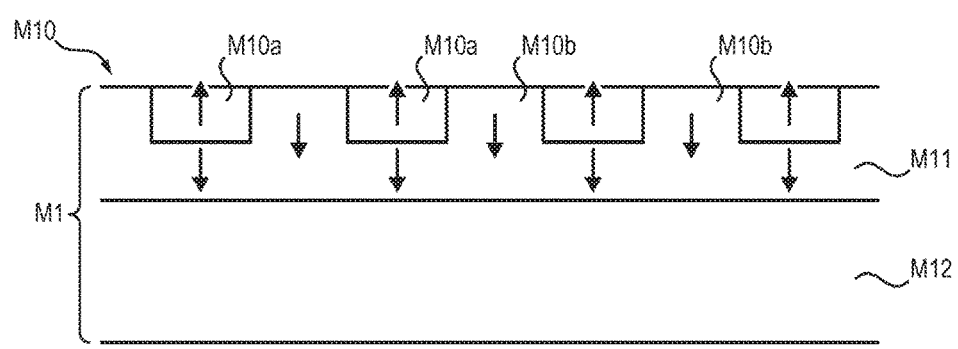

With reference to FIG. 4A, a master substrate M1 is used to order the nano- or microparticles before they are enclosed in a nonmagnetic matrix.

Said master substrate M1 exhibits a magnetically structured face, in other words a face M10 composed of a plurality of magnetic field microsources M10a, M10b, distributed according to a specified pattern.

The magnetization of the different microsources is indicated by an arrow.

In FIGS. 4A to 4D, the magnetically structured face M10 of the master substrate is flat.

However, in certain forms of implementation of the invention, it may be preferable to employ a master substrate having a face which is not flat but which instead has cavities or projections, so as to reproduce complementary projections or cavities in the film formed from the master substrate.

The master substrate may be manufactured by various techniques known to the skilled person.

More particularly, a thermo-magnetic patterning method or a topographical method of structuring may be employed, as described above.

In one nonlimiting example, which is illustrated in FIG. 4A, the master substrate is composed of a magnetically hard layer M11 of NdFeB, having a thickness of 5 μm, on a silicon support substrate M12, which is magnetically structured by thermo-magnetic patterning, so as to form regions M10a whose magnetization is opposite to that of the regions M10b.

In this master substrate, the intensity of the magnetic field and of the magnetic field gradient is at its maximum at the interfaces between the regions M10a and M10b which exhibit opposite magnetizations.

Consequently, nano- or microparticles exhibiting positive magnetic susceptibility are attracted toward these interfaces by the magnetophoretic force.

The master substrate, however, is not limited to this particular form, but instead may be composed of a soft or hard magnetic material structured by topography.

The master substrate may optionally be an electrical conductor.

When the master substrate has a surface structured by topography, in other words a non-flat surface, this particular topography may be exploited in order to impress a complementary form in the final film.

When the desire is to form a flat film from a master substrate of this kind, the substrate must be planarized beforehand, either by removal of material (for example, by means of chemomechanical polishing to remove the projections), or by addition of material (for example, by means of a deposition technique for filling in the cavities).

Figure 4B:
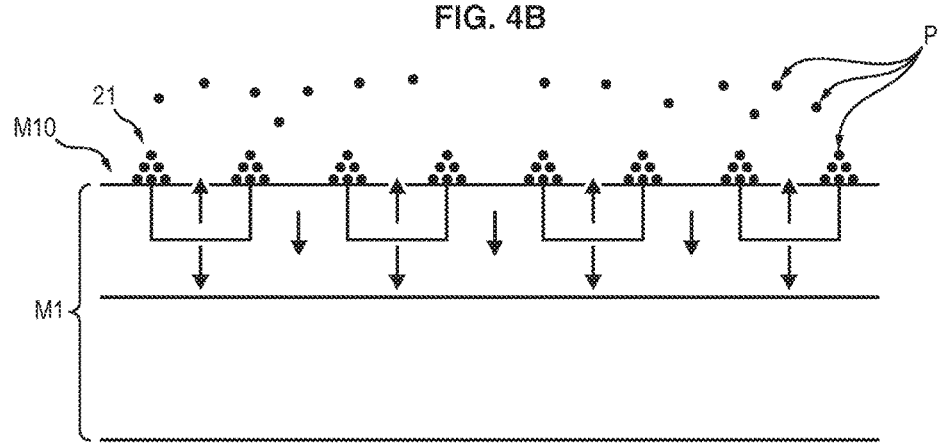

With reference to FIG. 4B, nano- or microparticles P of a hard magnetic material are sent to the magnetically structured face of the master substrate 1.

Under the effect of the attractive magnetophoretic force of the magnetically structured face of the master substrate, the particles P agglomerate at the edges of each of the microsources.

Insofar as the force decreases in line with the distance from the face of the master substrate, these agglomerates 21 generally exhibit a triangular or trapezoidal section, with a larger base on the side of the master substrate M1, which reduces with the distance.

In order to promote the ordering of the particles not only in one plane but also in a direction perpendicular to the master substrate, it is possible to apply simultaneously an external magnetic field having an appropriate direction.

During the sending of the particles, the master substrate is advantageously agitated so as to optimize the trapping of the particles at the edges of the magnetic field microsources.

Moreover, during or after this sending, a jet of dry gas can be projected, in order to promote the trapping of the particles at said edges and/or to remove untrapped particles before the deposition of the nonmagnetic matrix.

The particles are made of a hard magnetic material, which may be one of the materials from the list set out above.

Consequently, the application of an external magnetic field after the film has been formed will allow them to be magnetized permanently and thus will allow an autonomous magnetically structured film to be formed.

With reference to FIG. 4C, a matrix 22 made of a nonmagnetic material in the form of a thin layer is subsequently deposited on the agglomerated particles on the master substrate.

The thickness of the matrix 22 is typically between 100 nm and 5 mm.

The matrix is advantageously made of an elastomeric material, allowing the film to be given a certain flexibility.

According to preferred embodiments of the invention, the matrix is made of one of the following materials: polydimethylsiloxane (PDMS), epoxy resin, rubber, Bakelite, polymethyl methacrylate (PMMA), polystyrene (PS), photosensitive resin, parylene, oxides such as $SiO_2$ and $Al_2O_3$, metals such as Cu and Ag, and carbon materials such as graphite, DLCs, etc.

If necessary, the matrix 22 is left to harden or crosslink for the appropriate time.

The matrix, moreover, may advantageously be made of a transparent or translucent material.

The skilled person has the capacity to select an appropriate matrix from the products available on the market, according to the desired properties.

With reference to FIG. 4D, the film 2 composed of the matrix 22 and of the agglomerates 21 of particles which are magnetic with respect to the master substrate M1 is peeled off.

The master substrate for its part may be used again to manufacture a further film.

Therefore, although the master substrate necessitates the implementation of microfabrication techniques, and consequently carries a certain cost, it can be re-used indefinitely, and the manufacture of the magnetically structured film itself, which does not involve such complex and expensive techniques, employs only relatively inexpensive materials.

This method, moreover, is readily industrializable, and allows films of large surface area to be produced in large quantities at low cost.

According to one form of implementation of the invention, a layer of a material facilitating peeling of the film may be applied to the master substrate, before the particles are deposited, this layer remaining integral with the master substrate during the peeling operation.

Owing to the small size of the particles to be immobilized on the support, the ordered magnetic field microsources are preferably arranged directly on the surface of the support—or in its immediate vicinity—in contact with the sample, to provide maximum forces of attraction.

Multiwell Plate

Conventionally, titration plates comprising a plurality of wells (for example, 96 or 384 wells) are used in immunodetection assays.

In order to immobilize the complexes, a plate of this kind may be integrated with ordered magnetic field microsources as described above.

This integration may be obtained by producing the plate itself in a material adapted to form ordered magnetic field microsources, according to one of the methods described above. In that case the magnetic field microsources are placed preferably at the bottom of each of the wells.

According to another form of implementation, it is possible to insert a support with the size of each well inside said well, with said ordered magnetic field microsources being arranged on said support.

According to another embodiment, it is possible to produce a titration plate in which the wells do not have a bottom, and to bring a flat support, containing ordered magnetic field microsources arranged at the level of each well, beneath said plate, so as to constitute the impervious bottom of said wells.

The method is therefore compatible with the supports commonly employed in immunoassay, and so does not require any modification to existing laboratory apparatus.

Flat Support

According to one particularly advantageous embodiment of the invention, the support on which the complexes are immobilized is not a titration plate, but instead a flat support with a plurality of ordered magnetic microsources arranged on its surface.

A support of this kind may be produced by the various methods described above for microstructuring of magnetic layers.

Alternatively, said support may be produced by the Micro-Magnetic Imprinting method described above.

This manufacturing technique has the advantage of enabling the low-cost manufacture of a large quantity of supports, the only expensive item being the master substrate, which is infinitely reusable.

Moreover, with this technique, the support has the advantage that it can be made of a transparent or translucent material.

This property may in certain cases facilitate the detection and quantification by optical methods.

Hence it allows the support to be lit from below, allowing the coloring to be observed from the top of the support with a camera and filters whose selection is known to the skilled person.

On the other hand, this transparency may be a disrupting factor in the case, for example, of intense fluorescence, where there may be interference of the signals between contiguous sites.

It will therefore be possible to select the material of the support depending on the intended detection method.

When a flat support of this kind is used, the mixing of the molecule for detection, the magnetic particles, and the element capable of binding selectively to said molecule is carried out in a container, and then limited volumes of the mixture are withdrawn and deposited on said support in the form of a drop, as illustrated in FIG. 5.

The size of the drops is dependent on the volume deposited and on the hydrophilicity of the material of the support. This size is therefore adjustable, typically between 1 microliter and 200 microliters.

The ordered magnetic field microsources are advantageously spread over the surface of the support according to a regular pattern, so as to allow the capture of complexes irrespective of the region of the support on which the drop was deposited.

The site intended for each drop is preferably produced physically on the flat support, for example by local magnetic labeling, or chemically (rendering the surface of the support locally hydrophilic or hydrophobic), or else topographically, by a shallow trough made in the surface of the support. It is also possible for the site to be labeled visually to help the practitioner in locating it.

Unexpectedly, it has been shown that the rate of capture of magnetic beads was substantially higher in drops deposited on a flat support of this kind than in a solution deposited in a well of a titration plate.

Figure 6:
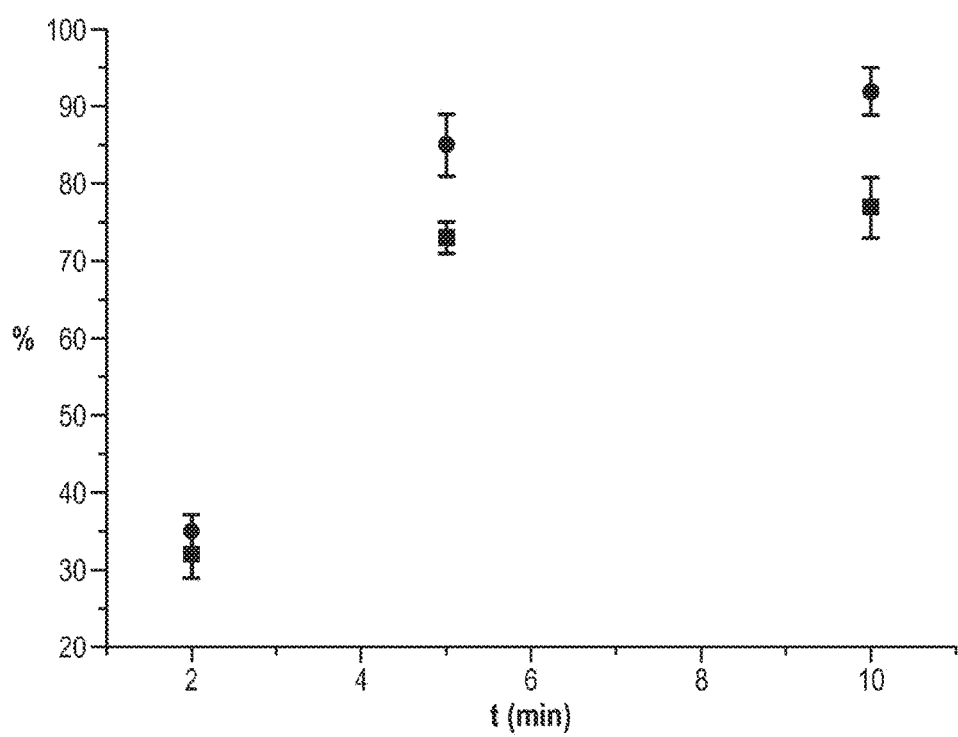
FIG. 6 presents a comparison of the percentages of beads captured on a flat support and in a titration well as a function of time.

FIG. 6 presents the percentage of beads with a diameter of 100 nm captured respectively in a drop (data represented by a disk), and the amount of beads of the same type captured in a well (data represented by a square).

After 10 minutes, 75% of the beads have been captured by the ordered magnetic field microsources disposed at the bottom of the titration well, while more than 90% of the beads have been recovered by the ordered magnetic field microsources disposed in the support receiving the drop.

This phenomenon is explained by the presence of a convection movement induced within the fluid by the conveying of the magnetic particles toward the ordered magnetic field microsources which capture them.

The speed of spread of the particles therefore obviates the need for any vibration device, which is necessary in conventional assays in order to accelerate the mixing of the solution.

Another advantage of the flat support relative to a conventional titration plate is that it allows more molecule capture sites to be provided for a given space taken up by the support.

Kinetics of Capture of Magnetic Nanoparticles by a Support Comprising Ordered Magnetic Field Microsources The kinetics and the efficacy of notable capture of magnetic nanoparticles by supports comprising ordered magnetic field microsources are due to hydrodynamic coupling between the particles.

The reason is that the magnetic particles closest to the surface of the support are attracted rapidly by the ordered magnetic field microsources, and their drag hydrodynamically entrains the movement of more distant particles toward the magnetic field microsources which, once they have reached the surface of the support, are attracted magnetically in their turn.

This coupling between magnetic forces and hydrodynamic entrainment results in the appearance of a fluidic convection current which agitates the fluid above the magnetic field microsources, thereby explaining the efficacy and the kinetics of long-distance capture of the nanoparticles, in spite of their small size.

This interpretation is justified by a theoretical model and by an experiment demonstrating the existence of this coupling.

In this experiment, the inventors visualized the movement of a fluid sample by virtue of nonmagnetic colored particles in suspension in a fluid deposited on a linear junction between two magnetized zones.

This junction simulates an element of a matrix of ordered magnetic field microsources produced by the Thermo-Magnetic Patterning technique described above.

It is at this junction that the highest magnetic field gradients are located.

Measurement of the movement and of the velocity of the beads (by a technique known as "particle tracking velocimetry") made it possible to reconstitute the movement and the speed of the fluid.

Figure 9:
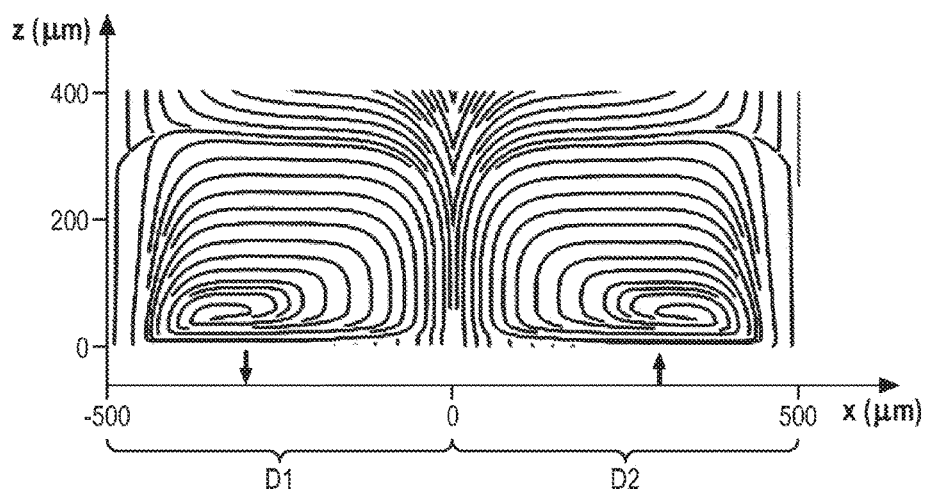
FIG. 9 represents the flow lines of a fluid containing magnetic particles which is contacted with a support comprising two magnetic domains magnetized in opposite directions.

In FIG. 9, which illustrates the current lines induced by the attraction of superparamagnetic nanoparticles in suspension above a junction between two magnetic domains D1, D2, the senses of magnetization of which are shown by arrows (where the axis z denotes the thickness of fluid above the junction), it is clearly apparent that two symmetrical vortices form rapidly on either side of the junction, and agitate the liquid over a distance of the order of several mm.

In the absence of magnetic microparticles, there is no ordered movement of the fluid in evidence.

The field of the speeds of the fluid measured corresponds, to an accuracy of 10%, to that calculated by the hydrodynamic-magnetic coupling model described above.

This coupling is manifested for concentrations of magnetic particles of more than $10^6$ particles/ml, this being effectively observed experimentally.

The formation of convection currents is intimately linked to the ordering of the magnetic field microsources.

Microfluidic System

According to another advantageous embodiment of the invention, the support may be a microfluidic system of "lab-on-chip" type.

The support in that case comprises a microchannel and a network of magnetic microsources arranged in an ordered way in at least one wall of said channel.

Said microchannel may be produced by the "Micro-Magnetic Imprinting" method described above.

In this case, as illustrated in FIGS. 7A to 7E, the magnetically structured face of the master substrate 1 is not flat, but instead has at least one projection or cavity, the inverse of which will be present on the film.

Figure 7A:
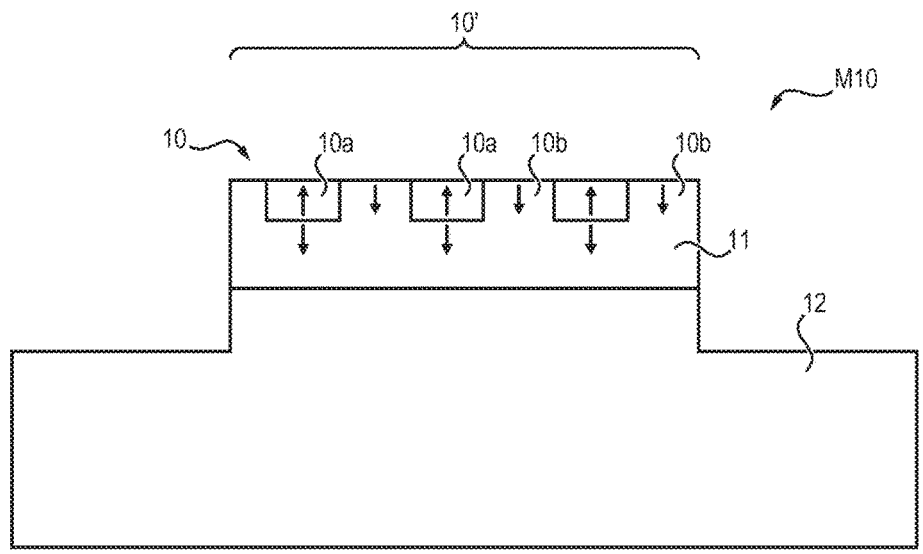

In the nonlimiting example illustrated in FIG. 7A, the magnetically structured face 10 of the master substrate 1 has a projection in relief 10', the surface of the projection being composed of a plurality of magnetic field microsources 10a, 10b.

For example, said projection may have a parallelepipedal form.

According to the intended applications, the remainder of the surface of the master substrate may also be magnetically structured, although it is also possible to envisage only the surface of the projection 10' being magnetically structured; in this latter case, the nano- or microparticles provided will undergo agglomeration only at the edges of the magnetic microsources constituting the surface of the projection 10', with the rest of the surface of the master substrate not retaining particles.

Figure 7B:
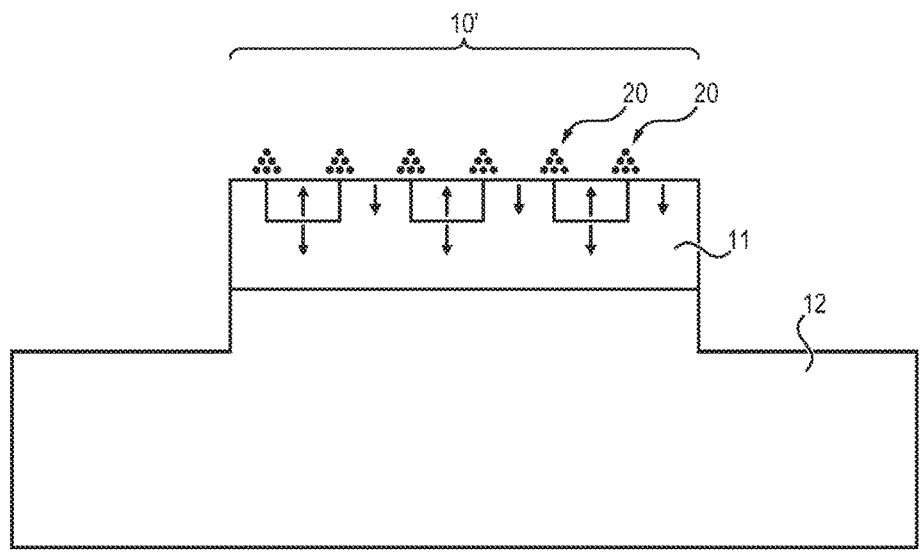

As explained above, the magnetic nano- or microparticles are provided on the master substrate, and undergo ordering and agglomeration into three-dimensional structures 20 at the edges of the magnetic field microsources 10a, 10b (FIG. 7B).

Subsequently, with reference to FIG. 7C, the nonmagnetic matrix 3 is deposited on the master substrate.

At the end of the peeling operation, the resulting film 4, which is illustrated in FIG. 7D, therefore has a cavity 40 complementary to the projection 10' of the master substrate.

Depending on the form of the raised area, the film thus comprises one or more wells, or one or more channels.

It is therefore possible to form a fluidic microchannel from a film of this kind.

For this purpose, as illustrated in FIG. 7E, all that need be done is for a flat film 4', or any other structure allowing formation of the fourth wall of the cavity 40, to be applied against said film 4.

Advantageously, said flat film 4' may also be manufactured according to the invention and may comprise three-dimensional magnetic structures 20' on its surface.

Accordingly, from films 4 and 4', a device 6 is formed that comprises a microchannel 60 having a magnetically structured surface on two opposite walls 61a and 61b.

A surface treatment may ensure the imperviosity of the two films.

For example, when the two films possess a PDMS matrix, the surfaces may be activated by an oxygen plasma.

By virtue of the presence of three-dimensional magnetic structures on the two faces 61a and 61b of the microchannel 61, the trapping of nano- or microparticles within a solution circulating in said microchannel is enhanced.

Of course, the nature of the magnetic particles, and also their distribution relative to the surface of each wall, may be identical for each of the two walls, or else may be different.

In a system of this kind, the mixture is injected at the inlet of the microchannel: the solution circulates in the microchannel, with the complexes being gradually immobilized on the bottom of the microchannel by the magnetic field microsources.

It is subsequently possible, optionally, to carry out a washing step to remove the residues of the solution, with the complexes remaining trapped magnetically by the microsources situated on the walls of the channel.

Example of Coupling of an Antibody to a Magnetic Particle (Commercial Dynabead Protocol)

As an indication, the coupling of an antibody to a magnetic bead may be performed according to the following procedure:

freshly suspending the beads by vortex agitation of a solution in which they are dispersed, withdrawing the desired amount of beads, removing the supernatant by means of a pipette and a magnet, adding the antibody in dilution in 0.01% PBS-Tween, carrying out incubation for 10 minutes at ambient temperature with stirring, removing the supernatant by means of a pipette and a magnet, resuspending the beads coupled to the antibody in 0.01% PBS-Tween.

Experimental Validations

One embodiment of the invention was validated in a sandwich-type antigen assay conducted under the following conditions:

The antigen for assay that was used for the purpose of this experiment was the (biotinylated) "core protein" of the hepatitis C virus; the capture antibody used was a monoclonal antibody specific for this protein (Pierce Hepatitis C Virus Core Antigen Monoclonal Antibody (C7-50)); superparamagnetic beads 100 nm in diameter and functionalized with protein A (fluidMAG-Protein A, Chemicell) were used; and, as detection antibodies, quantum dots functionalized with avidine (QD625, Invitrogen) were used.

In this experiment, the concentrations used were 1.3 nM for the capture antibody, $10^9$/ml for the superparamagnetic beads, and $10^{19}$/ml for the quantum dots.

In a single step, the quantum dots, the antibody-functionalized beads and the biotinylated antigen were placed on a flexible substrate comprising magnetic field microsources.

The duration of mixing/capture was set at 7 minutes.

After this time, the supernatant was removed and two washes were carried out with 50 µl of PBS.

Lastly, the amount of antigen was measured directly on the support by virtue of the fluorescence of the quantum dots.

Figure 8:
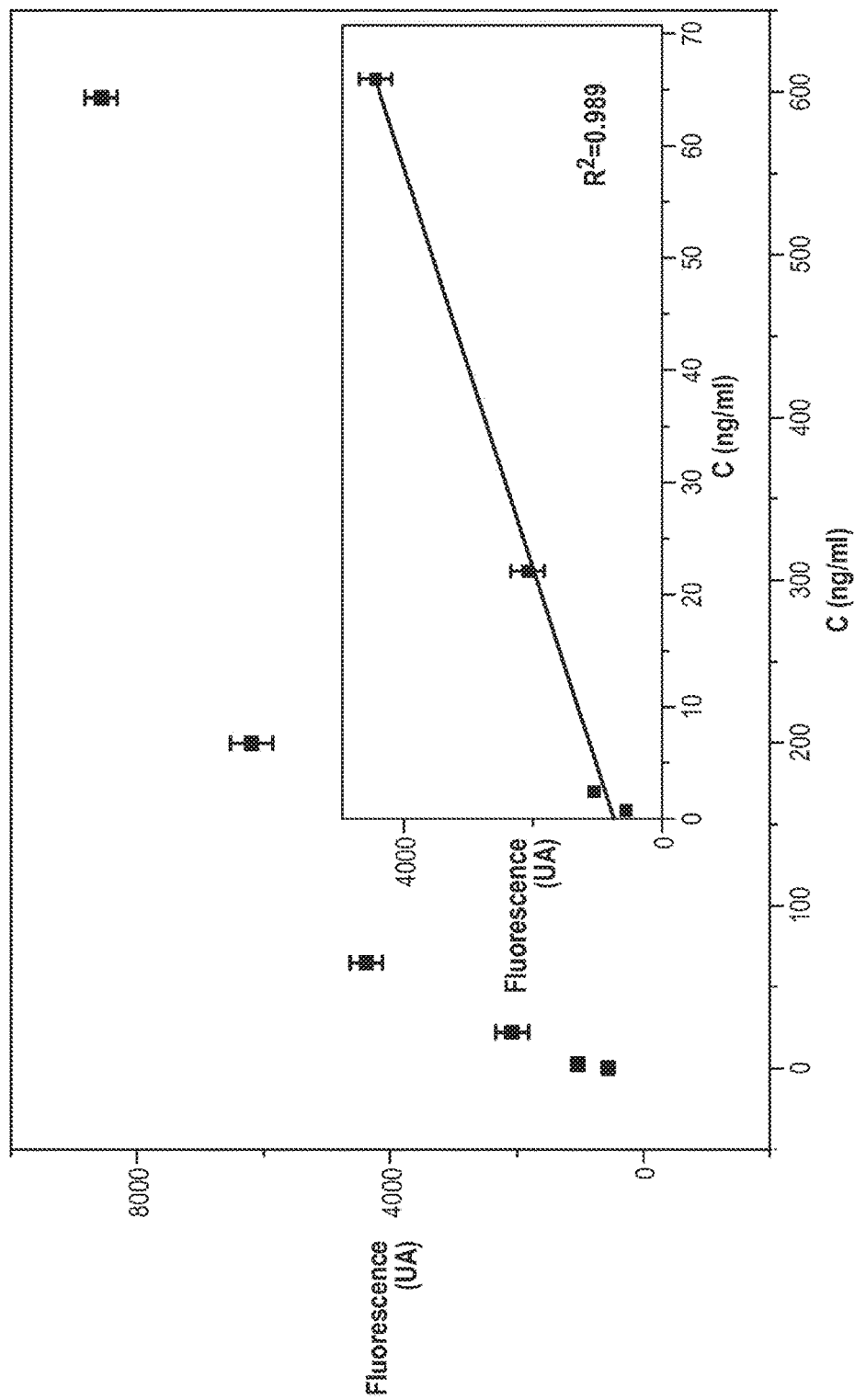
FIG. 8 is a plot of the fluorescence signal as a function of the amount of antigen obtained in experiments.

FIG. 8 illustrates the fluorescence (in arbitrary units [UA]) as a function of the concentration of antigen.

The whole assay was carried out in around ten minutes.

The detection limit is 10 pM, this being comparable to the limit in the commercially available ELISA assays conducted on this protein.

Beyond 5 nM, the assay was positive, but the response of the assay was saturated because of the camera used.

In any case, concentrations of this kind are well beyond clinical cases; moreover, it is possible if necessary to dilute the sample in order to repeat an assay.

Detection without Washing

The spatial organization of the ordered magnetic field microsources allows detection to be carried out with neither washing of the support nor labeling of the immunocomplexes.

For this purpose, all that need be done is to determine the fluorescence density at the surface of the ordered magnetic field microsources in the strong magnetic field gradient zones (specific signal) and in the weak magnetic field gradient zones (nonspecific signal).

This detection may be done by fluorescence, by focusing the image detection on the surface of the support containing the magnetic field microsources, or by disposing detectors on the surface of the support itself.

The following experiment demonstrates the feasibility of such detection.

Magnetic nanoparticles (50 nm, $10^9$ ml$^{-1}$) and nonmagnetic fluorescent nanoparticles (quantum dots, 30 nm, $10^9$ ml$^{-1}$) functionalized with biotin were mixed at low concentrations of avidine, which is a protein which binds quasi-irreversibly to four molecules of biotin.

This coupling mimics the formation of immunocomplexes: (magnetic nanoparticles)-(capture antibody)-(antigen)-(detection antibody)-(fluorescent label) or other.

After 10 minutes of incubation, a drop is deposited on the surface of a support comprising ordered magnetic field microsources, produced by the technique of Micro-Magnetic Imprinting, and this drop is observed using an optical fluorescence microscope 10 minutes later.

The microscope is focused on the support.

Figure 10A:
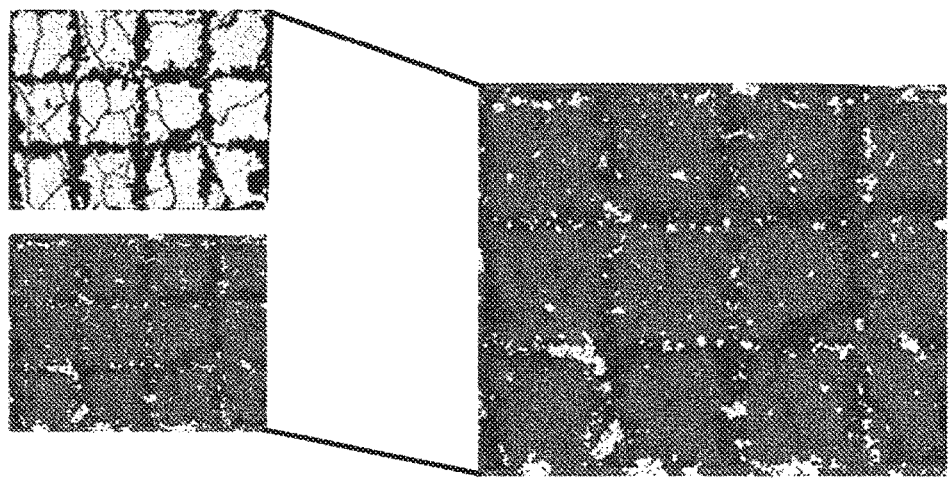
FIG. 10A shows the distribution of fluorescent complexes captured by magnetic particles at magnetic field microsources, as determined in experiments and observed by microscopy.

In FIG. 10A, the top-left image shows the structure of the support comprising the ordered magnetic field microsources, observed in phase contrast (the magnetic field microsources being arranged according to a grid which has a darker color than the rest of the matrix), while the bottom-left image shows the distribution of the biotinylated quantum dots at the surface of the support in the presence of biotinylated magnetic nanoparticles and of avidine, observed in fluorescence (the quantum dots have a light color in this image).

The superposition of the two images on the right in FIG. 10A shows the quantum dots obtained from specific interaction with the magnetic nanoparticles:

clearly apparent is that the quantum dots (with light color) are primarily aligned along the grid (of dark color) defined by the magnetic field microsources (specific signal), and therefore reproduce the pattern defined by the magnetic field microsources, with only a few quantum dots being located in zones situated within this grid (nonspecific signal).

In the absence of avidine, no pattern is visible.

The density of fluorescence in the zones of strong and weak magnetic field gradient was measured in the microscope images shown at A.

Figure 10B:
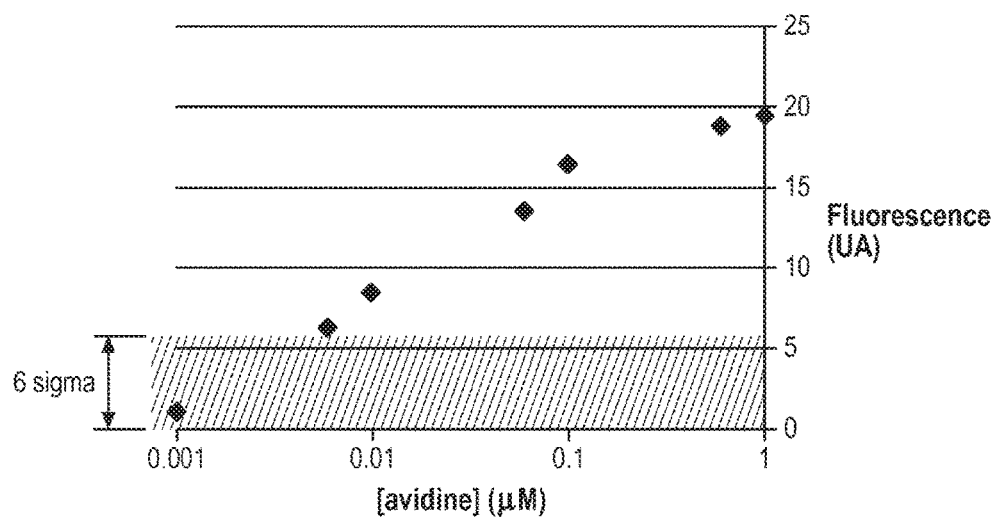
FIG. 10B illustrates the ratio between the specific signal and the nonspecific signal measured on microscopy images of the type of FIG. 10A.

FIG. 10B shows the change in the (specific signal)/(nonspecific signal) ratio, which is equal to the (specific fluorescence×area of the weak magnetic field gradient regions)/(nonspecific fluorescence×area of the strong magnetic field gradient regions) ratio, as a function of the concentration of avidine.

If there is no specific interaction, this ratio is 1. The hatched zone corresponds to the 6-sigma confidence interval. All points outside this zone are significant, with an error probability of less than $10^{-6}$.

A concentration of 50 nM is therefore detectable at the 99.9997% significance threshold (six sigmas).

The microstructuring of the ordered magnetic field microsources allows "specific" and "nonspecific" regions of interest to be defined. It may therefore be exploited for the purpose of simplifying detection.

It should be noted that magnetic field microsources disposed randomly would not allow this detection without washing.

REFERENCES

D. Issadore et al., Self-assembled magnetic filter for highly efficient immunomagnetic separation, Lab Chip, 2011, 11, 147
N. M. Dempsey et al., App. Phys. Lett. 90, 092509 (2007)
A. Walther et al., J. Magn. Mag. Mat. 321 (2009) 590
M. Kustov et al., J. App. Phys. 108, 063914 (2010)
F. Dumas-Bouchiat et al., App. Phys. Lett. 96, 102511 (2010)

The invention claimed is:

1. A method comprising capturing a molecule in a sample, wherein capturing said molecule comprises mixing said sample with magnetic particles, said particles being microparticles or nanoparticles, each of said magnetic particles being coupled to an element capable of binding selectively to said molecule for capture so as to form at least one complex, wherein said at least one complex comprises one of said magnetic particles, said element, and said molecule that is bound to said element, and immobilizing said at least one complex on a surface of a support, wherein said support contains ordered magnetic field microsources disposed close to said surface that is intended for contact with said at least one complex, wherein said ordered magnetic field microsources are sources of magnetic fields and are orderly distributed according to a specified pattern relative to said surface of said support that is intended for contact with said at least one complex and exhibit a specified magnetic orientation, and wherein the said orderly distribution of the ordered magnetic field microsources defines strong magnetic field gradient zones and weak magnetic field gradient zones causing each of said at least one complex to be immobilized on said surface of said support in at least one location of the specified pattern defined by the ordered magnetic field microsources.

2. The method as claimed in claim 1, wherein the ordered magnetic field microsources contained in the support are present in a form of ordered three-dimensional agglomerates of magnetized particles enclosed within a nonmagnetic matrix, wherein said magnetized particles, which constitute the ordered three-dimensional agglomerates, are made from a magnetic material selected from the group consisting of a hard magnetic material and a soft magnetic material, wherein said particles are selected from the group consisting of microparticles and nanoparticles.

3. The method as claimed in claim 1, wherein the ordered magnetic field microsources contained in the support are present in a form of magnetic microcoils enclosed within a nonmagnetic matrix, and wherein the microcoils are ordered according to a specified pattern.

4. The method as claimed in claim 2, wherein said nonmagnetic matrix is flexible.

5. The method as claimed in claim 2, wherein said nonmagnetic matrix is made of a material selected from the group consisting of a translucent material and a transparent material.

6. The method as claimed in claim 1, wherein the molecule for capture is an antigen and wherein the element capable of binding to said molecule is a receptor antibody for said antigen.

7. The method as claimed in claim 6, wherein a detection antibody is added to said mixture, wherein said antibody carries a label selected from the group consisting of a fluorescent label, a luminescent label, and a colorimetric label, wherein said label is capable of binding to the antigen bound to the antibody coupled to the magnetic particle.

8. The method as claimed in claim 1, wherein the molecule to be captured is an antibody and wherein the element capable of binding to said molecule is an antigen recognized by said antibody.

9. The method as claimed in claim 1, wherein the support comprises a titration plate, wherein the titration plate comprises a plurality of wells, wherein the ordered magnetic field microsources are arranged on a wall of each of said wells, and wherein the mixture is deposited in at least one of said wells.

10. The method as claimed in claim 1, wherein the support comprises a flat plate, said flat plate comprising a plurality of ordered magnetic field microsources, the mixture being deposited in the form of at least one drop on said support.

11. The method as claimed in claim 1, wherein the support comprises a microfluidic channel in which at least one of the walls comprises the ordered magnetic field microsources.

12. The method as claimed in claim 1, further comprising, after the immobilizing of said at least one complex on the support, washing said support to remove the sample, said at least one complex being retained on the support by the ordered magnetic field microsources.

13. The method of claim 1, further comprising detecting a molecule in said sample, wherein the method comprises, after having captured the molecule on the support detecting the molecule captured on the support using a technique selected from the group consisting of fluorescence, luminescence, colorimetry, electrochemistry, and radiometry.

14. The method as claimed in claim 13, wherein the detecting the molecule captured on the support is implemented directly after capturing the molecule, without washing the support between capturing the molecule and detecting the molecule.

15. The method as claimed in claim 13, further comprising washing the support between capturing the molecule and detecting the molecule, wherein washing the support removes the sample, and wherein the microsources retain the complexes on the support.

16. The method as claimed in claim 1, wherein the magnetic particles have a diameter of between 5 mn and 500 mn.

17. The method as claimed in claim 1, wherein said mixture of said sample with said magnetic particles has a concentration in magnetic particles higher than $10^6$ particles/ml.

* * * * *